United States Patent [19]

Jean et al.

[11] Patent Number: 5,640,962
[45] Date of Patent: Jun. 24, 1997

[54] PROCESS AND DEVICE FOR DETERMINING THE TOPOGRAPHY OF A REFLECTING SURFACE

[75] Inventors: Benedikt Jean, Sigmarszell; Thomas Bende, Mössingen; Michael Matallana-Kielmann, Tübingen-Hirshau, all of Germany

[73] Assignee: Technomed Gesellschaft für Med. und Med. Techn. Systeme mbH, Baesweiler, Germany

[21] Appl. No.: 495,461

[22] PCT Filed: Jan. 7, 1994

[86] PCT No.: PCT/EP94/00027

§ 371 Date: Jul. 21, 1995

§ 102(e) Date: Jul. 21, 1995

[87] PCT Pub. No.: WO94/16611

PCT Pub. Date: Aug. 4, 1994

[30] Foreign Application Priority Data

Jan. 21, 1993 [DE] Germany ............ 43 01 525.5
Mar. 19, 1993 [DE] Germany ............ 43 08 949.6
Jul. 29, 1993 [DE] Germany ............ 43 25 494.2

[51] Int. Cl.$^6$ .................... A61B 3/107; G01B 11/24
[52] U.S. Cl. ............ 128/664; 128/653.1; 128/665; 128/745; 351/211; 351/212
[58] Field of Search ............ 351/200, 206, 351/211, 212, 246; 128/653.1, 664, 665, 745

[56] References Cited

U.S. PATENT DOCUMENTS 3,598,478  8/1971  Townsley .
4,159,867  7/1979  Achatz et al. .
4,597,648  7/1986  Feldon .
4,772,115  9/1988  Gersten et al. .
4,863,260  9/1989  Gersten .
4,993,825  2/1991  Abe et al. .
5,009,498  4/1991  Gersten et al. .
5,214,456  5/1993  Gersten .
5,227,818  7/1993  El Hage .
5,513,642  5/1996  Ostrander .

FOREIGN PATENT DOCUMENTS 0076866    4/1983   European Pat. Off. .
WOA9109564 7/1991   WIPO .

Primary Examiner—Marvin M. Lateef
Assistant Examiner—Shawna J. Shaw
Attorney, Agent, or Firm—Henry M. Feiereisen

[57] ABSTRACT

A process is disclosed for determining the topography of a reflecting surface. A projection pattern is projected onto the surface and a thus formed mirror reflection pattern is detected and evaluated. In order to improve the correspondence of the structures of the reflection patterns with those of the projection patters, the projection pattern contains recognition marks which individualize the continuous black/white or light/dark areas. A color mark or hatching is particularly advantageous. In order to apply the projection pattern on the cornea of the eye (3), a projection body (17), for example a hollow cone, is used, with transparent rings (19) arranged in this side wall (18) and surrounded by a ring-shaped light source (20). A color video camera (26) is used as detector.

14 Claims, 2 Drawing Sheets

PROCESS AND DEVICE FOR DETERMINING THE TOPOGRAPHY OF A REFLECTING SURFACE

The invention refers to a process and apparatus for determining the surface topography of a reflecting surface according to the preamble of claims 1 to 13.

Processes of this type, especially for measuring the cornea based upon a Moiré pattern projection method are known under the designation video keratometry. What is meant thereby is the projection of the so-called placido disk, i.e. a pattern of concentric alternating black and white rings upon the human cornea. The reflections from the corneal surface are registered by a video camera for computation. Of particular interest are the distances or distortions of the structure of the reflection pattern compared to a standard of measurement.

In case of measuring a cornea, the standard of measurement is formed by a known surface which is required for a correct evaluation/assessment of the corneal surface. The analysis of stated distortions from the standard of measurement yields informations about the radius of the corneal curvature as well as deviations from a spherical surface, as encountered in astigmatism.

Processes of this type are known for example from U.S. Pat. Nos. 4,978,213, 4,863,260 and 4,772,115.

In this process, the association of the reflection pattern to the scanned-in projection rings has often proven difficult and resulted not infrequently in errors. The association becomes particular difficult when the corneal surface is defective and causes gaps in the reflection pattern of an initially closed ring that is projected upon the cornea. The erroneous association of unrelated structures of a reflection pattern to a particular scanned-in projection ring results in grave errors, for example in form of an incorrect determination of the corneal radius or in form of an incorrect determination of the distortions of the corneal surfaces from the desired spherical surface.

In addition to the imaging of a ring-shaped projection pattern, the use of a grid-shaped line pattern is known. This, however, could not eliminate the above-stated problems.

Moreover, hitherto conventional processes are extremely sensitive with regard to misalignments of the eye in the Z-axis, i.e. in the connection axis between the corneal apex and the image detection unit.

It is thus the object of the present invention to propose a process for determining the topography of a reflecting surface and especially of the cornea, which ensures an unambiguous and reliable association of the structures of the reflection pattern reflected from the surface to those of the scanned-in projection pattern.

Further, it is desired to provide a suitable device for carrying out the process.

This object is attained by a process and by a device based upon the above-stated type by the characterizing features of claims 1 and 13. The features recited in the subclaims enable additional advantageous further developments and improvements of the invention.

In accordance with the invention, at least three distinguishable recognition marks are used within the projection pattern projected onto the surface for characterizing the structures of the projection pattern. This can be achieved by e.g. an additional recognition mark which is distinguishable from black/white and bright/dark marks. This utilization of specially designated zones within the projection pattern generates together with e.g. bright and dark zones an additional criteria of association of the structures of the image pattern specularly reflected from the reflecting surface with regard to the projection pattern projected onto the surface. Certainly, the number of criteria of association is increased by employing several such recognition marks so that this association becomes further improved. When using at least three marks with colors that are distinguishable from each other, black-white marks can be omitted altogether.

In accordance with a particularly advantageous embodiment, at least one color marking is used as recognition mark. The provision of such color markings allows an easy association of the structures of the reflection pattern to the respective projection pattern. In particular, superimpositions of two marks are recognizable by the occurrence of a respective mixed color.

It would also be conceivable to use a different recognition mark, for example a hatching. Basically, attention must be paid only to the fact that the recognition marks, in case of a hatching the structures of this hatching, are recognizable in a projection pattern e.g. comprised of uniformly continuous black/white marks or bright/dark marks.

The process according to the invention for determining the topography of a reflecting surface is applicable in multifaceted, nearly all technical fields of application, like e.g. in spheres. In a particular application, this process is utilized for measuring the surface topography of the cornea of an eye.

Advantageously, this is accomplished by a projection body which is illuminated for example by a white light source and has transparent, preferably ring shaped zones of different colors. It is however easily possible to provide an arrangement of differently colored light sources, for example in form of an array of diodes.

In accordance with a preferred embodiment, a projection body in form of a hollow cone or a hollow ellipsoid with transparent rings, in particular color rings, is used in the side wall. The utilization of such hollow shapes which are arranged with their concave side facing towards the eye, the projection body can be designed with comparably small diameter relative to the Z-axis. The Z-axis is formed, as stated above, by the prolongation of the axis of the image detection unit relative to the surface being measured.

Preferably, an image detector in form of a color video camera is used. However, the use of a black/white camera together with respective color filters would certainly also be conceivable. In this case, the measurement of individual color rings is carried out sequentially with respective filter change.

Advantageously, the reflection signal from the corneal surface is measured integral in its intensity. This serves for compensation of fluctuations of the ambient illumination which are randomly distributed and mutually compensate each other in this fashion.

It is in particular recommended to automatically execute the signal processing in a processor-controlled evaluation unit with output monitor. In accordance with a particular advantageous embodiment, the results are outputted thereby in form of isoreflection lines which refer to those areas of the surface that have a same reflective power during the described measurement. Thus, the deviations from the standard of measurement are visible directly and without requiring any further interpretation of the measuring data. In order to immediately differentiate image points of measured values that are determined through computation, for example through interpolation, a different type of illustration, for example transparent in contrast to opaque may be selected.

With such an automated evaluation unit, a control of the projection unit is furthermore possible. This means, that all parameters of the projection unit with the respective results of the evaluation unit are automated or interactively optimized with regard to a greatest possible unambiguity of the surface topography.

It is in particular important in the described process to attain a good adjustment of the surface, for example the corneal surface, relative to the image detection unit in Z-direction. The image-forming qualities of the entire arrangement depend significantly on this distance. The adjustment in direction of the Z-axis is preferably carried out through scanning-in of at least two centering objects in the projection pattern at a particular angle between their respective projection axes. The intersection of both projection axes yields thereby the desired correct Z-position. A shift of this position in Z-direction is reflected in such an arrangement by a lateral shift of the reflected images of both centering objects relative to each other. Certainly, the centering objects can be marked in colors whereby a superimposition of both objects results advantageously in a mixed color.

A centering object can thereby be generated by a laser beam which extends at an angle relative to the Z-axis and intersects it in the desired position.

Also without correct alignment of the Z-position, the ensuing error can be corrected by the thus determined deviation from the desired position through computation by the evaluation method.

In case of a medical application, in particular for determining the surface topography of the corneal surface of an eye, a measuring device which operates according the stated process, can be coupled directly onto the operating microscope to enable the surgeon to recognize corneal areas having a deviation from the desired geometry and to immediately render respective treatment.

By using a high resolution camera together with a respective zoom optics, this technique may also be employed for measurement with a resolution in the micrometer range. Thus, the measurement of smallest changes in the roughness within smaller surface segments of the cornea is possible.

For forming a respective hollow ellipsoid during use of a static projection body, various processes are conceivable.

A possibility offers for example the so-called foil technique in which initially a color foil with circular, multicolored rings is formed, subsequently matched in form of a hollow ellipsoid to a projection head and finally fused in. A further possibility is the so-called sandwich technique or multilayer technique, in which rings are formed from several colored Plexiglas blocks and cut off by means of a lathe or milling unit to provide respective thickness and color. The rings are fixated on a negative form and glued together. This composite may also be produced through layered casting of plastics of different colors. Subsequently, this composite, for example on a lathe, is matched to the desired geometry.

In accordance with a third embodiment, a transparent Plexiglas blank with rings that are finely scribed in correspondence to their later position of the color ring. The entire blank is then colored black. In the grooved rings, the black color can then be removed and substituted by a respective transparent color.

An exemplified embodiment of the invention as well as the difficulties being solved with regard to the association between projection pattern and reflection pattern will now be illustrated in more detail in the following drawing and described with reference to the individual figures, in which FIG. 1 shows the reflection pattern of a projection pattern comprised of several concentric rings, in the event of a healthy cornea i.e. of spherical surface;

Figure 1:
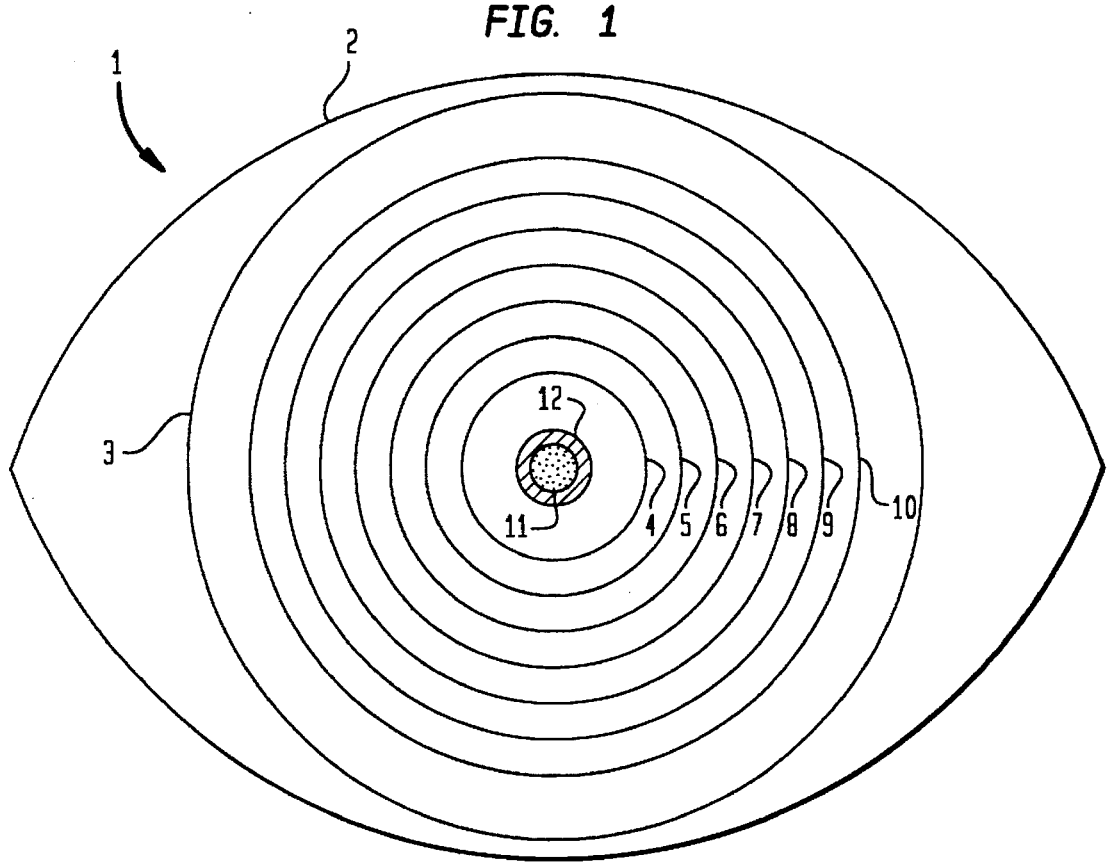

FIG. 1 shows schematically the image of an eye 1 of amygdaloid configuration 2 as registered by an image detection system of the above-described type. Depicted within the interior of the circumferential line 2 is the contour of the cornea 3. Several reflection rings 4 to 10 are shown concentric to the Z-axis (camera corneal apex). Located within the interior of these rings are two centering objects which are described in more detail further below. The distance as well as the concentric and circular arrangement of the rings 4 to 10 correspond to the reflected image of a healthy cornea with spherical surface.

It should be understood by persons skilled in the art that any reference to a reflection in connection with the present invention should mean a specular or mirror reflection.

Figure 2:
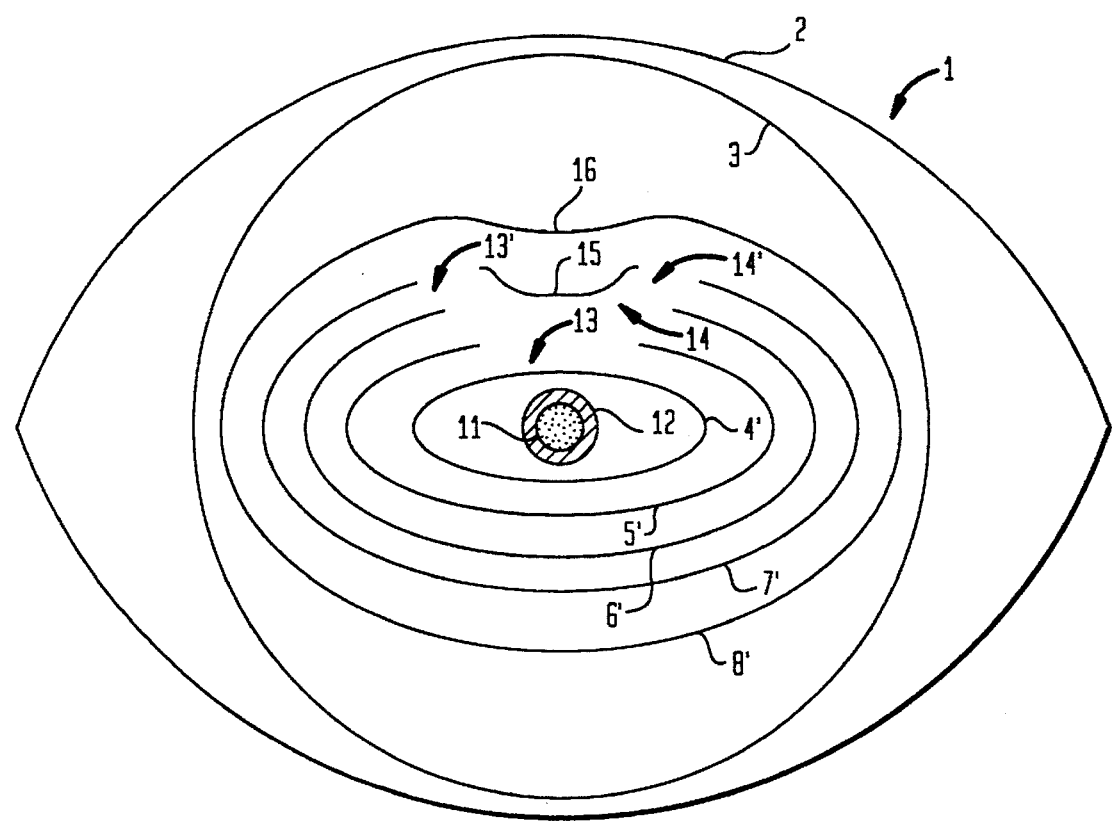
FIG. 2 shows an example of a comparable reflection pattern in the event of a cornea deviating from the spherical configuration.

In contrast thereto, FIG. 2 shows the corresponding image of a deformed cornea, i.e. in case of astigmatism. The structures 4' to 8' represent also a mirror reflection pattern of absolute concentric and circular projection rings. Their image is deformed by a non-spherical corneal surface. In part, the images 5', 6' of the respective and originally closed projection rings even have gaps 13, 14 and 13', 14' while other structures 7', 8' show significant dents 15, 16. In a normal black/white photography, which cannot be illustrated in the drawing any different, the zone 15 of the structure 7' cannot unequivocally be associated to a respective projection ring. This zone 15 could be associated to the projection rings as formed by the reflection rings 5, 6 or 7 of a healthy cornea (FIG. 1). Because of the ambiguity in this association the interpretation of these data to determine the surface topography is necessarily erroneous.

In accordance with the invention, the rings 4 to 10 and the structures 4' to 8' are colored by a respective coloration of the projection pattern. Thus, even in the event of a significantly deformed mirror reflection image (see FIG. 2), a unequivocal association is possible.

Figure 3:
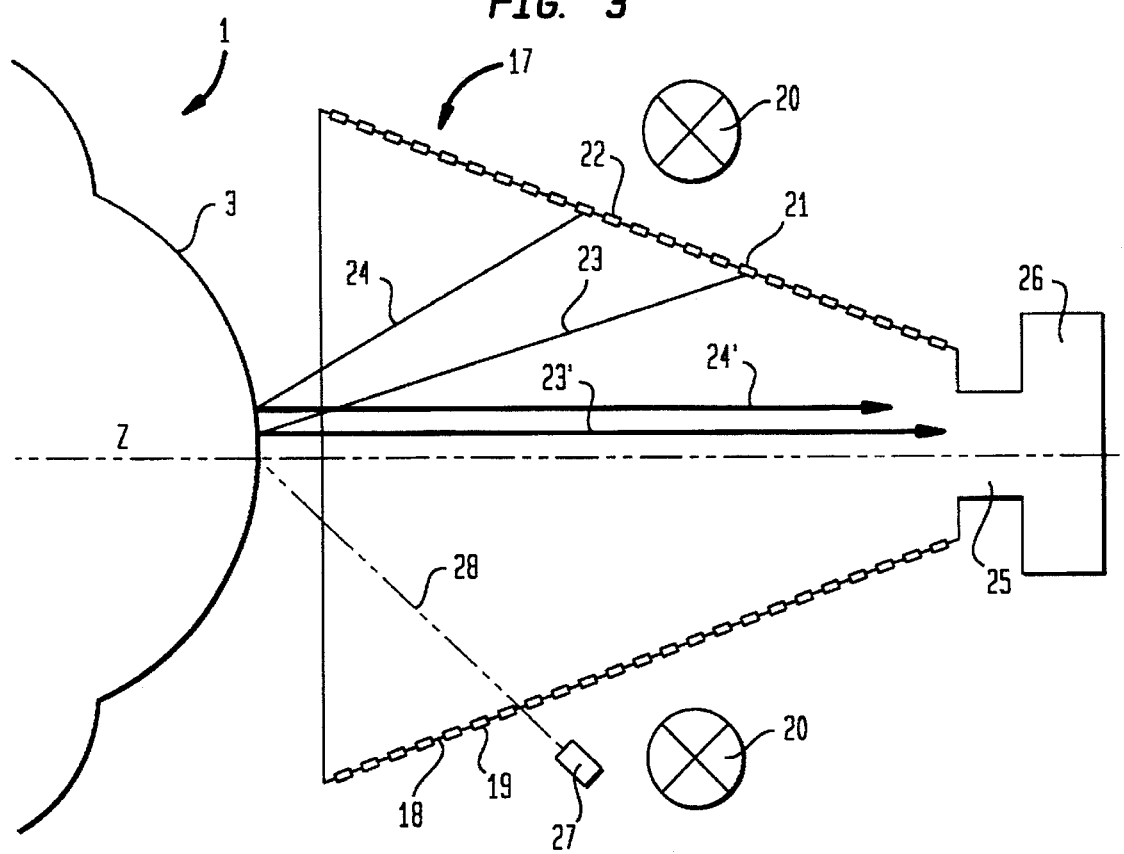
FIG. 3 shows a schematic illustration of an arrangement for carrying out the process according to the invention with static projection body.

FIG. 3 shows a schematic, sectional illustration of an arrangement for carrying out the measuring process according to the invention. Positioned in front of the eye 1 with the arched cornea 3 is a projection body 17.

The projection body 17 includes a cone-shaped hollow body, with a side wall 18 having ring-shaped, transparent and differently colored passages 19. The cone-shaped projection body 17 is illuminated from outside by a ring-shaped neon tube 20. The showing of two light beams emitting from differently colored ring-shaped passages 21, 22 and symbolized by lines 23, 34 illustrates the projection of the ring structures upon the cornea. The beams 23' and 24' reflected from the cornea 3 radiate through a pinhole diaphragm at the narrower end of the cone-shaped projection body 17 and form an image in an image detector 26.

Figure 4:
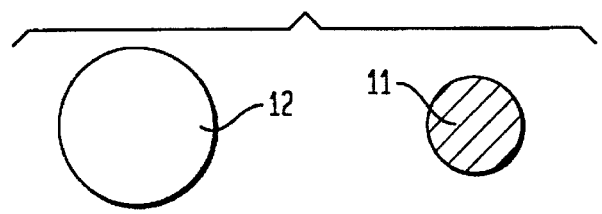
FIGS. 4 to 6 show the images of two centering objects at different position of the cornea in direction of the Z-axis relative to the image detector.
Figure 5:
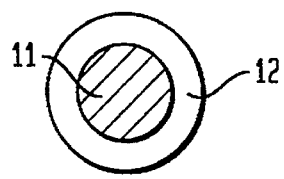
Figure 6:
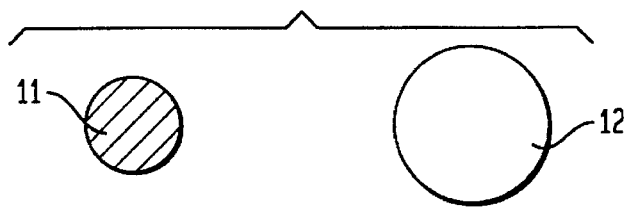

The centering objects 11, 12, which are scanned-in for generating the images in FIGS. 4 to 6 at a certain angle between their projection axes in a plane which coincides also with the Z-axis, have a different relative orientation according to the position of the cornea upon the Z-axis with regard to the intersection of the projection axes. FIGS. 4 to 6 show the images of the centering objects with the corneal surface 3, positioned in front of this point of intersection, positioned precisely in the intersection, and positioned behind the point of intersection. The arrangement of the images of the centering objects 11, 12 allows the determination of the Z-position of the corneal surface 3 and its evaluation.

FIG. 3 illustrates that one projection axis is formed by a laser beam 28 which is generated by a laser unit 27. The laser beam 28 forms the centering object 11 e.g. upon the cornea whereby the laser unit 27 may be arranged outside the projection body, with the projection body including a small aperture in its wall for passage of the laser beam 28 which then intersects the Z-axis in the desired point. After alignment in Z-direction, the laser unit can be turned off.

LIST OF USED REFERENCE NUMERALS

1 Eye
2 Outline
3 Corneal Surface
4 Ring
5 Ring
6 Ring
7 Ring
8 Ring
9 Ring
10 Ring
11 Centering Object
12 Centering Object
13 Gap
14 Gap
15 Dent
16 Dent
17 Projection Body
18 Side Wall
19 Passage
20 Neon Tube
21 Passage
22 Passage
23 Beam
24 Beam
25 Pinhole Diaphragm
26 Image Detector
27 Laser Unit
28 Laser Beam

We claim:

1. A process for determining the topography of a reflecting surface, comprising the steps of:
   projecting a projection pattern exhibiting at least three recognition marks of different colors that are distinguishable from black and white onto a surface to form a mirror reflection pattern created through reflections from the surface; and
   evaluating the mirror reflection pattern by comparing the mirror reflection pattern with the projection pattern and assigning recognition marks of same color of the mirror reflection pattern and the projection pattern to each other to enable a characterization of the surface.

2. A process according to claim 1 wherein at least one recognition mark is formed as hatching of the respective zone of the projection pattern.

3. A process according to claim 1 wherein the projection pattern is generated by a projection body with transparent passages of different colors.

4. A process according to claim 3 wherein the projection body is formed as hollow cone or as hollow ellipsoid with transparent rings in its side wall.

5. A process according to claim 1 wherein the evaluating step includes using a color video camera as detector for forming an image of the mirror reflection pattern.

6. A process according to claim 1 wherein the evaluating step includes using a black/white camera together with one or more respective color filters for reading the mirror reflection pattern formed on the surface.

7. A process according to claim 1, and further comprising the step of compensating fluctuations of ambient illumination by integrally measuring the intensity of the mirror reflection pattern through attenuating ambient lighting.

8. A process according to claim 5 wherein the evaluating step includes transmitting an output signal of the image detector to a processor-controlled evaluation unit, with isorefractions lines of the measured surface being illustrated upon an output monitor.

9. A process according to claim 8 wherein the evaluation unit includes a control unit for optimizing the projection pattern with regard to an unequivocal surface topometry.

10. A process according to claim 1 wherein the position of the surface being measured along the Z-axis, i.e. along the prolongation of the axis of the image detector, is detected by scanning n at least two centering objects at an angle between their projection axes, whereby the point of intersection of both projection axes indicates the correct Z-position.

11. A device for determination of the topography of a reflecting surface, comprising:
    a projection unit for projecting a projection pattern exhibiting at least three recognition marks of different colors that are distinguishable from black and white onto a surface to form a mirror reflection pattern created through reflection from the surface;
    an image detection unit for detecting the mirror reflection pattern; and
    an evaluation unit comparing the mirror reflection pattern with the projection pattern and assigning recognition marks of same color of the mirror reflection pattern and the projection pattern to each other to enable a characterization of the surface.

12. A device according to claim 11 wherein the projection unit has a projection body in form of a hollow cone or hollow ellipsoid, with transparent rings in the wall and an external illumination unit.

13. A device according to claim 12, and further comprising a laser unit associated to the projection unit for projecting a centering object.

14. A device according to claim 13 wherein the projection body has a wall farmed with an aperture for passage of laser beams emanating from the laser unit.

* * * * *